US006558693B1

(12) United States Patent
Knap et al.

(10) Patent No.: US 6,558,693 B1
(45) Date of Patent: May 6, 2003

(54) ANIMAL FEED ADDITIVES

(75) Inventors: Inge Helmer Knap, Farum (DK); Lene Venke Kofod, Uggerlose (DK); Anders Ohmann, Bronshoj (DK)

(73) Assignee: Novozymes, A/S, Bagsvaerd (DK)

( * ) Notice: Subject to any disclaimer, the term of this patent is extended or adjusted under 35 U.S.C. 154(b) by 0 days.

(21) Appl. No.: 09/059,771

(22) Filed: Apr. 14, 1998

Related U.S. Application Data

(63) Continuation of application No. PCT/DK96/00443, filed on Oct. 22, 1996.

(30) Foreign Application Priority Data

Nov. 6, 1995 (DK) ............................................. 1233/95

(51) Int. Cl.⁷ ............................................. A23K 7/165
(52) U.S. Cl. ................... 424/442; 494/94.2; 494/94.61; 426/53
(58) Field of Search ................................. 424/438, 442, 424/94.2, 94.61, 444, 477; 426/2, 52, 53; 435/175, 179, 187, 207, 208

(56) References Cited

U.S. PATENT DOCUMENTS 5,474,922 A * 12/1995 Dorreich et al. ............ 435/200

FOREIGN PATENT DOCUMENTS

| WO | WO 88/01506 | 3/1988 |
| WO | 94/14952 | * 7/1994 |

OTHER PUBLICATIONS

G. Annison, Feed Enzymes, pp. 193–201, Oct. 15, 1995.
Bryden et al., Proc. Aust. Poult. Sci. Sym., p. 115 (1994).
G. Annison, Proc. Aust. Poult. Sci. Sym., p. 126–129 (1995).
Patent Abstract of Japan 58–201949 (Nov. 25, 1983).
van de Vis et al., Carbohydrate Polymers, vol. 16, pp. 167–187 (1991).
Beudeker et al., Enzymen en Koolydraten Symposium, pp. 8–18 (Dec. 1, 1988).
JP58–201949 Patent Abstract of Japan vol. 8 #41 (C–211)(1478) Nov. 1983.*

* cited by examiner

*Primary Examiner*—Neil S. Levy
(74) *Attorney, Agent, or Firm*—Elias J. Lambiris

(57) ABSTRACT

The present invention relates to animal feed additives comprising galactanase enzymes. More specifically the invention relates to animal feed additives comprising a arabinogalactan endo-1,4-β-galactosidase and/or an arabinogalactan endo-1,3-β-galactosidase.

37 Claims, 1 Drawing Sheet

ANIMAL FEED ADDITIVES

CROSS-REFERENCE TO RELATED APPLICATIONS

This application is a continuation application of PCT/DK96/00443 filed Oct. 22, 1996 and claims priority under 35 U.S.C. 119 of Danish application 1233/95 filed Nov. 6, 1995, the contents of which are fully incorporated herein by reference.

TECHNICAL FIELD

The present invention relates to animal feed additives comprising galactanase enzymes. More specifically the invention relates to animal feed additives comprising a arabinogalactan endo-1,4-β-galactosidase and/or an arabinogalactan endo-1,3-β-galactosidase.

BACKGROUND ART

Traditionally animal feed diets for e.g. pigs and poultry are mainly based on cereals and soybean meal. However, the use of alternative products such as peas, beans, sunflower meal, rapeseed meal, lupines, cereal by-products and sugarbeet pulp has received increasing interest in recent years. In some of these products, e.g. sunflower meal, rapeseed meal, lupines, cereal by-products and sugarbeet pulp, low digestibility often limits their inclusion in appreciable quantities in animal feed diets. This low digestibility is associated with the composition of the carbohydrate fraction in these products, which mainly consists of non-starch polysaccharides. Non-starch polysaccharides are not degraded in the small intestine by the digestive enzymes of monogastric animals, and hence do not offer their full energy potential to the animal. Hydrolysis of these polysaccharides are known to solve two problems, one of animal welfare and the other relating to an improved economy in production.

Feed enhancing enzymes are enzymes that by improving feed digestibility are able to increase the efficiency of the feed utilization. Feed enhancing enzymes function by enhancing the digestibility of feed components. This enhancement may e.g. be brought about by degradation of poly- and oligosaccharides in cereals and vegetable proteins.

Established feed enhancing enzymes include α-galactosidases, phytases, β-glucanases, proteases, cellulases and xylanases. However, the use of galactanases and β-galactosidases as feed enhancing enzymes has never been suggested.

SUMMARY OF THE INVENTION

It has now been found that a certain group of enzymes designated galactanases are particularly beneficial for incorporation into animal feed, in particular when incorporated together with one or more other feed enhancing enzymes.

Accordingly, in its first aspect, the present invention provides animal feed additives comprising effective amounts of galactanase enzymes.

In another aspect the invention provides a method of improving the energy uptake from an animal diet, which method comprises supplementation of the animal feed additive of the invention to monogastric animals.

In yet another aspect, the invention provides a process for pre-treatment of animal feed, by which process the animal feed is subjected to the action of a galactanase enzyme.

BRIEF DESCRIPTION OF THE DRAWINGS

The present invention is further illustrated by reference to the accompanying drawing, in which.

DETAILED DISCLOSURE OF THE INVENTION

Animal Feed Additives

Figure 1:
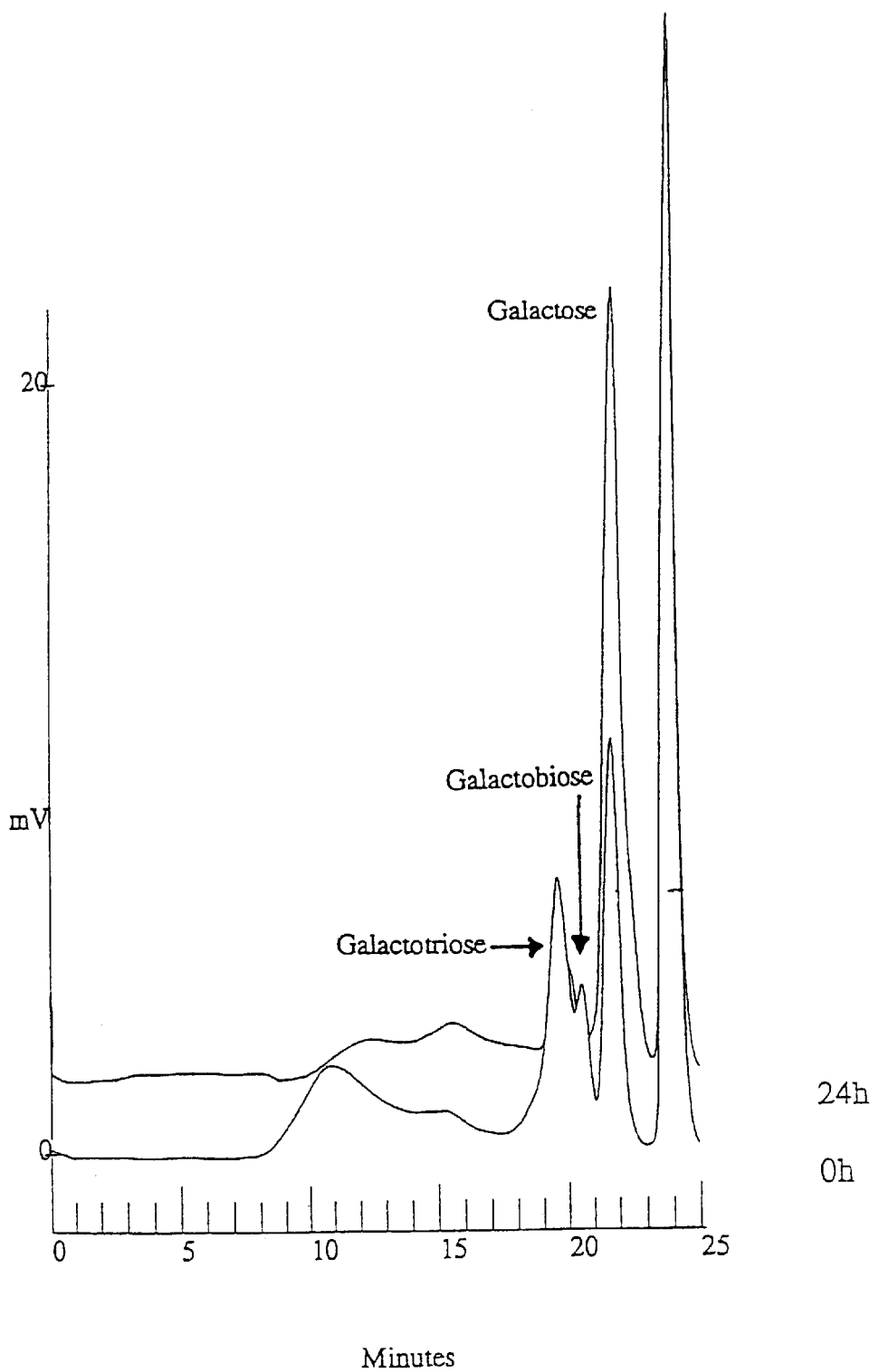
FIG. 1 shows the degradation of galactan by a galactanase and a lactase.

The present invention provides an animal feed additive comprising an effective amount of a galactanase enzyme. In a preferred embodiment, this galactanase enzyme is arabinogalactan endo-1,4-β-galactosidase (EC 3.2.1.89). In another preferred embodiment, the galactanase enzyme is arabinogalactan endo-1,3-β-galactosidase (EC 3.2.1.90). In a third preferred embodiment the animal feed additive comprises effective amounts of arabinogalactan endo-1,4-β-galactosidase and arabinogalactan endo-1,3-β-galactosidase.

In the context of this invention, an animal feed additive is an enzyme preparation comprising a feed enhancing enzyme (feed enzyme) and suitable carriers and/or excipients, and which enzyme preparation is provided in a form that is suitable for being added to animal feed. The animal feed additive of the invention may be prepared in accordance with methods known in the art and may be in the form of a dry or a liquid preparation. The enzyme to be included in the preparation may optionally be stabilized in accordance with methods known in the art. Stabilized enzyme preparations are also known as protected or stabilized enzyme systems.

In a specific embodiment the animal feed additive of the invention is a granulated enzyme product which may readily be mixed with feed components, or more preferably, form a component of a pre-mix. The granulated enzyme product may be coated or un-coated. The particle size of the enzyme granulates preferably is compatible with that of feed and pre-mix components. This provides a safe and convenient means of incorporating enzymes into feeds.

In another specific embodiment, the animal feed additive of the invention is a stabilized liquid composition, which may be an aqueous or oil-based slurry. The liquid composition may optionally be added to the animal feed composition after pelleting of this composition.

In another preferred embodiment, the present invention provides an animal feed additive, which additive additionally comprises an effective amount of one or more feed enhancing enzymes, in particular feed enhancing enzymes selected from the group consisting of β-galactosidase, in particular lactase, α-galactosidase, phytase, β-glucanase, mannanase, xylanase, protease, cellulase, or other hydrolases.

In its most preferred embodiment, the present invention provides an animal feed additive comprising a galactanase and a lactase only. In animal feed, polysaccharides such as galactan and arabino-galactanan are attached to rhamnogalacturan, a major constituent of the pectin matrix. Galactanase is able to cleave those bindings, resulting in monosaccharides of galactose, dimer of galactose (gal-gal) and various polysaccharides. Only galactose is directly metabolizable. By adding lactase, the dimer of galactose becomes hydrolysed, resulting in more monosaccharides of galactose, and a better feed utilization.

Microbial Sources

The enzymes employed according to the present invention may be obtained from any available source. Preferably the enzyme is of microbial origin, in particular of bacterial, of fungal or of yeast origin.

The enzyme may be derived from the source in question by use of any suitable technique. In particular, the phytase enzyme may be obtained by fermentation of a microorganism in a suitable nutrient medium, followed by isolation of the enzyme in question by methods known in the art.

Alternatively, the enzyme may be obtained by recombinant DNA techniques. In this way the enzyme may be obtained by general methods known in the art, e.g. isolating a DNA fragment encoding the enzyme in question; combining the DNA fragment with an appropriate expression signal in an appropriate plasmid vector; introducing the plasmid vector into an appropriate host (i.e. an *Escherichia coli,* or a member of the genus Bacillus, Aspergillus, or Streptomyces), either as an autonomously replicating plasmid or integrated into the chromosome; cultivating the host organism under conditions leading to expression of the enzyme; and recovering of the enzyme in question from the culture medium.

The broth or medium used for culturing may be any conventional medium suitable for growing the host cell in question, and may be composed according to the principles of the prior art. The medium preferably contain carbon and nitrogen sources and other inorganic salts. Suitable media, e.g. minimal or complex media, are available from commercial suppliers, or may be prepared according to published receipts, e.g. the American Type Culture Collection (ATCC) Catalogue of strains.

After cultivation, the enzyme is recovered by conventional methods for isolation and purification proteins from a culture broth. Well-known purification procedures include separating the cells from the medium by centrifugation or filtration, precipitating proteinaceous components of the medium by means of a salt such as ammonium sulphate, and chromatographic methods such as e.g. ion exchange chromatography, gel filtration chromatography, affinity chromatography, etc.

The enzyme-containing fermentation broth is preferably treated by means of both filtration and ultra-filtration prior to being used according to the present invention. Also, the enzymes in question may be incorporated as one or more monocomponent preparations or as complex enzyme preparations.

The galactanase enzyme contemplated according to the present invention may be derived from any available source. In a preferred embodiment the galactanase enzyme is derived from a filamentous fungus. Preferably the filamentous fungus is an Ascomycotina (e.g. the genera belonging to Loculomycetes, Discomycetes, Plectomycetes, Hemiascomycetes, Pyrenomycetes and Gymnoascales). In more preferred embodiments the fungus is an Ascomycete belonging to the Plectomycetes, more specifically Eurotiales, Trichocomaceae, or Aspergillus, or an Ascomycete belonging to Pyrenomycetes, more specifically Sordariales, or Chaetomiaceae, or the filamentous fungus is an Ascomycete belonging to mitosporic Pyrenomycetes, more specifically Humicola or Myceliophthora. In other preferred embodiments the filamentous fungus is a Basidiomycete, in particular a Basidiomycete belonging to Hymenomycetes (Dacrymycetales, Auriculariales, Cantharellales, Tulasnellales, Agaricales and Aphyllophorales), more specifically Aphyllophorales or Polyporaceae, more specifically Meripilus.

In most preferred embodiments, the galactanase enzyme is derived from a strain of Aspergillus, in particular *Aspergillus aculeatus* and *Aspergillus niger,* a strain of Bacillus, in particular *Bacillus subtilis* var. *amylosacchariticus,* a strain of Humicola, in particular *Humicola insolens,* a strain of Meripilus, in particular *Meripilus giganteus,* a strain of Myceliophthora, in particular *Myceliophthora thermophilum,* a strain of Penicillium, in particular *Penicillium citrium,* or a strain of Thermomyces, in particular *Thermomyces lanuginosus.*

Bacterial galactosidases are available from strains of *E. coli,* and from strains of Bacillus, in particular *Bacillus stearothezmophilus* and *Bacillus subtilis.* Fungal galactosidases are available from strains of Neurospora, Rhizopus and Aspergillus. Galactosidases also are available from yeasts, in particular from strains of *Saccharomyces cereviciae,* and from strains of *Saccharomyces oleaginosus.* In a preferred embodiment of the invention, the galactosidases are derived from a strain of *Aspergillus oryzae,* or a strain of *Aspergillus ficuum,* a strain of *Aspergillus aculeatus,* or a strain of *Aspergillus niger.*

The phytase enzyme may be derived from a fungal strain, in particular a strain of Aspergillus, e.g *Aspergillus niger, Aspergillus oryzae, Aspergillus ficuum, Aspergillus awaznori, Aspergillus nidulans* and *Aspergillus terreus.* Most preferred is a phytase enzyme derived from a strain of *Aspergillus niger* or a strain of *Aspergillus oryzae.* The phytase enzyme may also be derived from a bacterial strain, in particular a strain of Bacillus or a strain of Pseudomonas. Preferably the phytase enzyme is derived from a strain of *Bacillus subtilis.* Finally, the phytase enzyme may be derived from a yeast, in particular a strain of Kluveromzyces or a strain of Saccharomyces. Preferably the phytase enzyme is derived from a strain of *Saccharomyces cerevisiae.*

The β-glucanase enzyme may be derived from a strain of Aspergillus, in particular *Aspergillus aculeatus,* a strain of Humicola, in particular *Humicola insolens,* a strain of Thermomyces, in particular *Thermomyces lanuginosus,* or a strain of Trichoderma.

The xylanolytic enzyme may be derived from a strain of Aspergillus, a strain of Bacillus, in particular *Bacillus agaradherens* or *Bacillus pumilus,* a strain of Dictyoglomus, a strain of Humicola, a strain of Rhodothermus, a strain of Thermotoga, a strain of Thermomyces, in particular *Thermomyces lanuginosus,* or a strain of Trichoderma.

In the context of this invention "an enzyme derived from" encompasses an enzyme naturally produced by the particular strain, either recovered from that strain or encoded by a DNA sequence isolated from this strain and produced in a host organism transformed with said DNA sequence.

Method of Improving Energy Uptake

In another aspect, the invention relates to the use of the animal feed additive of the invention for improving the energy uptake from the diet supplied to monogastric animals.

In the context of this invention, monogastric animals include poultry, in particular broiler chicks, layers and turkeys, pigs, in particular piglets, and young calves.

According to this method, the animal feed additive of the invention is supplemented to the monogastric animal before or simultaneously with the diet. Preferably, the animal feed additive of the invention is supplemented to the monogastric animal simultaneously with the diet. In a more preferred embodiment, the animal feed additive is added to the diet in the form of a granulate or a stabilized liquid.

In another preferred embodiment, the diet comprises substantial amounts of leguminous, in particular soybean, lupine, peas and/or beans, and crucifera, in particular rapeseed.

In yet another preferred embodiment, the diet additionally comprises substantial amounts of cereals, preferably barley, wheat, rye, maize, rice and/or sorghum.

The feed enhancing enzymes should be applied in amounts adequate for degradation of the indigestible polysaccharides. It is at present contemplated that the enzyme is administered in an, amount corresponding to an activity in the range of from about 0.01 to about 10 mg enzyme protein per kg of animal feed, preferably of from about 0.1 to about 5 mg enzyme protein per kg of animal feed.

Pre-treatment of Animal Feed

In another aspect, the invention provides a process for pre-treatment of animal feed, by which process the animal feed is subjected to the action of a galactanase enzyme. Preferably the galactanase enzyme is an arabinogalactan endo-1,4-β-galactosidase or arabinogalactan endo-1,3-β-galactosidase.

In a preferred embodiment of the invention, the process further comprises treatment of the animal feed with an effective amount of one or more enzymes selected from the group consisting of β-galactosidase, in particular lactase, α-galactosidase, phytase, β-glucanase, and/or xylanase.

EXAMPLES

The invention is further illustrated with reference to the following examples which are not intended to be in any way limiting to the scope of the invention as claimed.

Example 1
Degradation of Galactan Hydrolysis Products by Lactase

Galactan was isolated from soy according to the procedure described by Labavitch et al. [*J. Biol. Chem.* 1976 251 5904–5910]. To a 1% solution of the isolated soygalactan in 0.1 M sodium acetate buffer pH 5.0, a galactanase (endo-1,4-β-galactosidase, obtained from *Aspergillus aculeatus* according to WO 92/13945, see in particular Example 3), was added, and incubated overnight at 30° C. After heat-inactivation of the galactanase, 10 ml of a 1% solution of sumilactase (Sumilact™, Lot. No. 40303-01, Available from Shinihon, Japan), was added to 1 ml of galactan degradation products, and incubation took place overnight at 30° C.

The degradation was monitored by High Performance Size Exclusion Chromatography as described by Christgau et al. [*Curr. Genet.* 1995 27 135–141], FIG. 1. This FIGURE shows that the hydrolysis products, resulting from the action of galactanase, are further degraded by the action of lactase. Thus, the lactase increases the amount of galactose, which is digestible, and significantly decreases the amount of galactobiose and higher oligomers and polymers, which are undigestible.

Example 2
True Metabolizable Energy

Using a bioassay for True Metabolizable Energy (TME) in feedstuffs, described by Sibbald [Sibbald I R; *Poultry Science* 1976 55 303–308], and modified by Dale & Fuller [Dale N and Fuller H L; *Poultry Science* 1984 63 1008–1012], the effects of a galactanase (endo-1,4-β-galactosidase, obtained according to WO 92/13945, see in particular Example 3), a lactase enzyme (Sumilact™, Lot. No. 40303-01, Available from Shinihon, Japan), and a mixture containing both enzymes, on the energy uptake from an animal feed composition, were examined.

In these experiments, the feed composition of the basal diet was soy bean meal. Galactanase was included at a dosage of 0.2 g/kg (Experiment A) or 1.0 g/kg (Experiment B) soy bean meal, and the lactase was included at a dosage of 0.1 g/kg (Experiment A) or 0.5 g/kg (Experiment B) soy bean meal.

In Experiment A, a total of 34 adult roosters were used, and in Experiment B, a total of 42 adult roosters were used. Prior to the experiments, the birds were starved for 21 hours to empty their digestive tracts. At the start of the experiment, the roosters were individually weighed and then force fed the appropriate amount of feed-stuff. After feeding, the birds were returned to cages, and excreta collected.

Exactly 48 hours from the force feeding, the birds were weighed again, and the voided excreta was collected quantitatively. The excreta was frozen, freeze dried, allowed to reach equilibrium with the atmospheric moisture, weighed, and grounded. Samples of ground feed and excreta, respectively, were assayed for gross energy using a calorimeter. Feed samples were assayed for dry matter. The results, determined as the difference between the energy of the feed supplied and the energy of the voided excreta, is presented in Tables 1 and 2, below.

TABLE 1

True Metabolizable Energy (TME)

| Treatments | Dosage (g/kg) | Number of animals (N) | TME (kcal/kg)/ improvement |
|---|---|---|---|
| Basal diet (B) | — | 8 | 3152 (a) |
| B + lactase | 0.1 | 9 | 3039 (b)/ −3.6% |
| B + galactanase | 0.2 | 9 | 2849 (c)/ −9.6% |
| B + lactase + galactanase | 0.1 + 0.2 | 8 | 3281 (a)/ +4.1% |

Values with different subscripts are significantly different (P < 0.05)

TABLE 2

True Metabolizable Energy (TME)

| Treatments | Dosage (g/kg) | Number of animals (N) | TME (kcal/kg)/ improvement |
|---|---|---|---|
| Basal diet (B) | — | 11 | 3003 (b) |
| B + lactase | 0.5 | 11 | 3006 (b)/ +0.1% |
| B + galactanase | 1.0 | 9 | 3058 (b)/ +1.8% |
| B + lactase + galactanase | 0.5 + 1.0 | 11 | 3212 (a)/ +7.0% |

Values with different subscripts are significantly different (P < 0.05)

Example 3
Apparent Metabolizable Energy

The effects of the enzymes on the nutritive value of basal diet were assessed using a classical apparent metabolizable energy (AME) assay to estimate the amount of dietary energy available to the bird. The AME study was conducted with an experimental basal diet containing sorghum (64%) and soy bean meal (30%).

Commercial broiler chickens (Inghamm™ IM98) were raised from hatch to 24 days of age in a floor pen in a controlled-temperature shed. The birds were given commercial starter feed for 21 days then commercial finisher feed. The chickens were weighed in groups of five and transferred to 48 metabolism cages located in another room in the same shed. Experimental diets were fed for seven days (days 1–7). The first three days (days 1–3) enabled the chickens to adapt to the cages and the feeds. Feed intake was measured during this period. During the following four days (days 4–7) feed intake was measured and all excreta collected and dried. Moisture content of excreta collected on day 5 was determined by overnight drying at 90° C. Each diet was given to 25 birds.

Dry matter (DM) contents of samples of sorghum, pelleted feeds, and milled feeds were determined by overnight drying at 105° C. Gross energy (GE) values of excreta and milled feeds were measured with a Parr isoperibol bomb calorimeter. Nitrogen contents of feed and excreta samples were measured by Kjeltec methods of digestion, distillation and titration.

In this experiment galactanase was included at a dosage of 6.7 ml/kg feed, and the lactase was included at a dosage of 3.3 ml/kg feed.

The results, determined as the difference between the energy of the feed supplied and the energy of the voided excreta, is presented in Table 3, below.

TABLE 3

Apparant Metabolizable Energy (AMEn)

| Treatments | Dosage (ml/kg feed) | Number of animals (N) | AMEn (MJ/kgDM)/ improvement |
|---|---|---|---|
| Basal diet (B) | — | 125 | 12.18 $^{bc}$ |
| B + lactase | 3.3 | 125 | 12.07 $^{c}$/ −0.9% |
| B + galactanase | 6.7 | 125 | 12.36 $^{abc}$/ +1.5% |
| B + lactase + galactanase | 3.3 + 6.7 | 125 | 12.65 $^{a}$/ +3.9% |

Values with different subscripts are significantly different (P < 0.05)

What is claimed is:

1. An animal feed which comprises (a) an animal feed carrier and/or excipient, (b) an endogalactanase in an amount between about 0.01 mg and about 200 mg endogalactanase per kg of feed, and (c) a lactase.

2. The animal feed of claim 1, wherein the endogalactanase is an arabinogalactan beta-1,4-endogalactosidase.

3. The animal feed of claim 1, wherein the endogalactanase Is an arabinogalactan beta-1,3-endogalactosidase.

4. The animal feed of claim 2, further comprising an arabinogalactan beta-1,3-endogalactosidase.

5. The animal feed of claim 1, further comprising at least one enzyme selected from the group consisting of alpha-galactosidase, beta-galactosidase, beta-glucanase, phytase, and xylanase.

6. The animal feed of claim 2, further comprising at least one enzyme selected from the group consisting of alpha-galactosidase, beta-galactosidase, beta-glucanase, phytase, and xylanase.

7. The animal feed of claim 3, further comprising at least one enzyme selected from the group consisting of alpha-galactosidase, beta-galactosidase, beta-glucanase, phytase, and xylanase.

8. The animal feed of claim 4, further comprising at least one enzyme selected from the group consisting of alpha-galactosidase, beta-galactosidase, beta-glucanase, phytase, and xylanase.

9. The animal feed of claim 1, wherein the amount is between about 0.1 mg and about 10 mg endogalactanase per kg of feed.

10. The animal feed of claim 1, further comprising legumes.

11. The animal feed of claim 10, wherein the legumes are soybean, lupine, peas and/or beans.

12. The animal feed of claim 1, further comprising crucifera.

13. The animal feed of claim 12, wherein the crucifera is rapeseed.

14. The animal feed of claim 10, further comprising crucifera.

15. The animal feed of claim 1, further comprising cereal.

16. The animal feed of claim 15, wherein the cereal is barley, wheat, rye, maize, rice and/or sorghum.

17. An animal feed which comprises (a) an animal feed carrier and/or excipient, (b) an endogalactanase in an amount between about 0.01 mg and about 200 mg endogalactanase per kg of feed and (c) soybean.

18. The animal feed of claim 17, wherein the endogalactanase is an arablnogalactan beta-1,4-endogalactosidase.

19. The animal feed of claim 17, wherein the endogalactanase is an arabinogalactan beta-1,3-endogalactosidase.

20. The animal feed of claim 18, further comprising an arabinogalactan beta-1,3-endogalactosidase.

21. The animal feed of claim 17, further comprising at least one enzyme selected from the group consisting of alpha-galactosidase, beta-galactosidase, beta-glucanase, phytase, and xylanase.

22. The animal feed of claim 21, wherein the at least one enzyme comprises a lactase.

23. The animal feed of claim 21, wherein the at least one enzyme consists of a lactase.

24. The animal feed of claim 18, further comprising at least one enzyme selected from the group consisting of alpha-galactosidase, beta-galactosidase, beta-glucanase, phytase, and xylanase.

25. The animal feed of claim 24, wherein the at least one enzyme comprises a lactase.

26. The animal feed of claim 24, wherein the at least one enzyme consists of a lactase.

27. The animal feed of claim 19, further comprising at least one enzyme selected from the group consisting of alpha-galactosidase, beta-galactosidase, beta-glucanase, phytase, and xylanases.

28. The animal feed of claim 27, wherein the at least one enzyme comprises a lactase.

29. The animal feed of claim 27, wherein the at least one enzyme consists of a lactase.

30. The animal feed of claim 20, further comprising at least one enzyme selected from the group consisting of alpha-galactosidase, beta-galactosidase, beta-glucanases phytase, and xylanase.

31. The animal feed of claim 30, wherein the at least one enzyme comprises a lactase.

32. The animal feed of claim 30, wherein the at least one enzyme consists of a lactase.

33. The animal feed of claim 17, wherein the amount is between about 0.1 mg and about 10 mg endogalactanase per kg of feed.

34. The animal feed of claim 17, further comprising crucifera.

35. The animal feed of claim 34, wherein the crucifera is rapeseed.

36. The animal feed of claim 17, further comprising cereal.

37. The animal feed of claim 36, wherein the cereal is barley, wheat, rye, maize, rice and/or sorghum.

* * * * *